(12) United States Patent
Denyer et al.

(10) Patent No.: US 8,967,140 B2
(45) Date of Patent: Mar. 3, 2015

(54) CONTROLLING DRUG DELIVERY APPARATUS

(75) Inventors: Jonathan Stanley Harold Denyer, Chichester (GB); Anthony Dyche, Hayling Island (GB)

(73) Assignee: Profile Respiratory Systems Limited, West Sussex (GB)

( * ) Notice: Subject to any disclaimer, the term of this patent is extended or adjusted under 35 U.S.C. 154(b) by 1206 days.

(21) Appl. No.: 09/781,610

(22) Filed: Feb. 12, 2001

(65) Prior Publication Data

US 2001/0022279 A1    Sep. 20, 2001

(30) Foreign Application Priority Data

Feb. 11, 2000 (GB) .................................. 0003197.1

(51) Int. Cl.
| | | |
|---|---|---|
| *A61M 16/00* | (2006.01) | |
| *A61M 15/00* | (2006.01) | |
| *B05D 7/14* | (2006.01) | |
| *B65D 83/06* | (2006.01) | |
| *A61B 5/08* | (2006.01) | |
| *A61B 5/087* | (2006.01) | |
| *A61B 5/00* | (2006.01) | |

(Continued)

(52) U.S. Cl.
CPC .............. *A61B 5/087* (2013.01); *A61B 5/4839* (2013.01); *A61M 15/0045* (2013.01); *G06F 19/3462* (2013.01); *G07F 17/0092* (2013.01); *A61B 5/0816* (2013.01); *A61J 1/065* (2013.01); *A61J 1/067* (2013.01); *A61J 1/14* (2013.01); *A61J 7/0481* (2013.01); *A61M 11/06* (2013.01); *A61M 2205/52* (2013.01); *A61M 2205/6018* (2013.01); *A61J 2200/30* (2013.01); *A61J 2205/50* (2013.01); *A61J 2205/60* (2013.01); *A61J 2205/70* (2013.01)

USPC ............ 128/203.12; 128/203.15; 128/200.16; 600/538

(58) Field of Classification Search
CPC .......... A61L 2/22; A61L 9/14; G06F 19/3418
USPC ............. 128/200.16, 203.12, 203.15, 203.27, 128/203.26, 203.28, 200.14, 200.23, 128/205.23, 202.22; 600/538
See application file for complete search history.

(56) References Cited

U.S. PATENT DOCUMENTS

| | | |
|---|---|---|
| 3,741,208 A | 6/1973 | Jonsson et al. |
| 3,991,304 A | 11/1976 | Hillsman |

(Continued)

FOREIGN PATENT DOCUMENTS

| | | |
|---|---|---|
| DE | 40 37 653 A1 | 6/1992 |
| DE | 4422710 C1 | 9/1995 |

(Continued)

OTHER PUBLICATIONS

Jonathan Stanley Harold Denyer, et al., "Breathing Patterns in Adult Patients," ISAM FOCUS SYMPOSIUM: Aerosol Therapy With Small Volume Nebulizers: Laboratory to Bedside; Sep. 4-5, 1996, Tours, France.

(Continued)

*Primary Examiner* — Elizabeth Houston
*Assistant Examiner* — Michael Mendoza (57) ABSTRACT

A drug package comprising a plurality of drug vials containing drugs for delivery to a patient in a drug delivery device; and a data carrier including drug treatment information for use by the drug delivery apparatus.

4 Claims, 9 Drawing Sheets

(51) Int. Cl.
   *G06F 19/00* (2011.01)
   *G07F 17/00* (2006.01)
   *A61J 1/06* (2006.01)
   *A61J 1/14* (2006.01)
   *A61J 7/04* (2006.01)
   *A61M 11/06* (2006.01)

(56) References Cited

U.S. PATENT DOCUMENTS

| | | | |
|---|---|---|---|
| 4,533,082 A | 8/1985 | Maehara et al. | |
| 4,617,557 A * | 10/1986 | Gordon | 340/309.7 |
| 4,819,629 A | 4/1989 | Jonson | |
| 4,832,012 A | 5/1989 | Raabe et al. | |
| 4,984,158 A * | 1/1991 | Hillsman | 128/200.14 |
| 5,020,527 A * | 6/1991 | Dessertine | 128/200.14 |
| 5,104,374 A | 4/1992 | Bishko et al. | |
| 5,167,506 A | 12/1992 | Kilis et al. | |
| 5,237,987 A * | 8/1993 | Anderson et al. | 128/204.18 |
| 5,261,601 A | 11/1993 | Ross et al. | |
| 5,267,174 A | 11/1993 | Kaufman et al. | |
| 5,283,133 A | 2/1994 | Tsutsumi et al. | |
| 5,284,133 A | 2/1994 | Burns et al. | |
| 5,328,035 A | 7/1994 | Duyvesteyn et al. | |
| 5,333,106 A | 7/1994 | Lanpher et al. | |
| 5,358,058 A | 10/1994 | Edlund et al. | |
| 5,363,842 A * | 11/1994 | Mishelevich et al. | 128/200.14 |
| 5,404,871 A * | 4/1995 | Goodman et al. | 128/200.14 |
| 5,408,443 A | 4/1995 | Weinberger | |
| 5,437,270 A * | 8/1995 | Braithwaite | 128/203.15 |
| 5,452,711 A * | 9/1995 | Gault | 128/200.14 |
| 5,483,953 A * | 1/1996 | Cooper | 128/200.22 |
| 5,505,195 A * | 4/1996 | Wolf et al. | 128/203.15 |
| 5,507,277 A | 4/1996 | Rubsamen et al. | |
| 5,509,404 A | 4/1996 | Lloyd et al. | |
| 5,522,385 A | 6/1996 | Lloyd et al. | |
| 5,549,106 A | 8/1996 | Gruenke et al. | |
| 5,551,416 A * | 9/1996 | Stimpson et al. | 128/200.14 |
| 5,562,550 A * | 10/1996 | Chartrand | 473/131 |
| 5,584,468 A | 12/1996 | Meglino et al. | |
| 5,590,648 A * | 1/1997 | Mitchell et al. | 600/301 |
| 5,593,390 A * | 1/1997 | Castellano et al. | 604/187 |
| 5,626,144 A | 5/1997 | Tacklind et al. | |
| 5,655,523 A * | 8/1997 | Hodson et al. | 128/203.12 |
| 5,657,236 A | 8/1997 | Conkright | |
| 5,657,748 A * | 8/1997 | Braithwaite | 128/203.15 |
| 5,685,291 A * | 11/1997 | Marsh | 128/200.15 |
| 5,694,920 A | 12/1997 | Abrams et al. | |
| 5,743,250 A | 4/1998 | Gonda et al. | |
| 5,755,218 A | 5/1998 | Johansson et al. | |
| 5,772,074 A | 6/1998 | Dial et al. | |
| 5,809,997 A | 9/1998 | Wolf | |
| 5,819,726 A | 10/1998 | Rubsamen et al. | |
| 5,823,179 A | 10/1998 | Grychowski et al. | |
| 5,852,590 A | 12/1998 | de la Huerga | |
| 5,890,016 A * | 3/1999 | Tso | 710/64 |
| 5,925,021 A | 7/1999 | Castellano et al. | |
| 5,928,775 A | 7/1999 | DiChiara, Jr. et al. | |
| 5,963,453 A | 10/1999 | East | |
| 6,012,454 A * | 1/2000 | Hodson et al. | 128/203.15 |
| 6,032,085 A | 2/2000 | Laurent et al. | |
| 6,082,544 A * | 7/2000 | Romick | 206/531 |
| 6,085,740 A * | 7/2000 | Ivri et al. | 128/200.16 |
| 6,116,233 A | 9/2000 | Denyer et al. | |
| 6,119,684 A | 9/2000 | Noehl et al. | |
| 6,142,146 A | 11/2000 | Abrams et al. | |
| 6,148,815 A | 11/2000 | Wolf | |
| 6,158,431 A * | 12/2000 | Poole | 128/203.12 |
| 6,167,302 A | 12/2000 | Millot | |
| 6,192,876 B1 | 2/2001 | Denyer et al. | |
| 6,196,219 B1 * | 3/2001 | Hess et al. | 128/200.21 |
| 6,202,642 B1 * | 3/2001 | McKinnon et al. | 128/200.23 |
| 6,224,560 B1 | 5/2001 | Gazula et al. | |
| 6,273,085 B1 * | 8/2001 | Eisele et al. | 128/203.15 |
| 6,315,719 B1 * | 11/2001 | Rode et al. | 600/300 |
| 6,318,361 B1 * | 11/2001 | Sosiak | 128/200.14 |
| 6,328,035 B1 | 12/2001 | Wakefield et al. | |
| 6,328,699 B1 * | 12/2001 | Eigler et al. | 600/486 |
| 6,358,058 B1 | 3/2002 | Strupat et al. | |
| 6,418,924 B1 * | 7/2002 | Poley et al. | 128/200.14 |
| 6,421,650 B1 * | 7/2002 | Goetz et al. | 705/3 |
| 6,435,175 B1 | 8/2002 | Stenzler | |
| 6,571,790 B1 * | 6/2003 | Weinstein | 128/200.19 |
| 6,584,971 B1 | 7/2003 | Denyer et al. | |
| 7,451,760 B2 | 11/2008 | Denyer et al. | |
| 2003/0205229 A1 | 11/2003 | Crockford et al. | |

FOREIGN PATENT DOCUMENTS

| | | |
|---|---|---|
| DE | 44 18 968 | 12/1995 |
| DE | 69400623 T2 | 2/1997 |
| DE | 19702362 A1 | 1/1998 |
| DE | 19755672 A1 | 6/1999 |
| EP | 0 667 168 | 2/1994 |
| EP | 0615913 A1 | 3/1994 |
| EP | 0 627 266 | 6/1994 |
| EP | 0827733 A1 | 3/1998 |
| EP | 0923957 A1 | 6/1999 |
| EP | 0 952 127 B1 | 3/2000 |
| GB | 2 077 444 | 6/1981 |
| GB | 2 294 402 | 10/1995 |
| GB | 2343122 A | 3/2000 |
| JP | 8010330 A | 1/1996 |
| JP | 10504729 A | 5/1998 |
| WO | WO 92/17231 * | 10/1992 |
| WO | WO 93/20486 | 10/1993 |
| WO | WO94/07607 | 4/1994 |
| WO | WO 94/17370 | 8/1994 |
| WO | WO96/13292 | 5/1996 |
| WO | WO 96/38396 | 12/1996 |
| WO | WO97/29851 | 2/1997 |
| WO | WO 97/14393 | 4/1997 |
| WO | WO 97/15339 | 5/1997 |
| WO | WO97/48431 | 6/1997 |
| WO | WO 97/32271 | 9/1997 |
| WO | 9738750 A1 | 10/1997 |
| WO | WO 98/55017 | 12/1998 |
| WO | WO 99/04043 | 1/1999 |
| WO | WO 99/08235 | 2/1999 |
| WO | WO 99/10029 | 3/1999 |
| WO | 9925404 A1 | 5/1999 |
| WO | WO 99/25110 | 5/1999 |
| WO | WO 00/64346 | 11/2000 |
| WO | WO 00/65996 | 11/2000 |
| WO | WO 01/08106 | 2/2001 |

OTHER PUBLICATIONS

European Search Report, Oct. 2, 2007.

* cited by examiner

CONTROLLING DRUG DELIVERY APPARATUS

BACKGROUND OF THE INVENTION

1. Field of the Invention

This invention relates to the control of drug delivery apparatus, for example such apparatus for delivering a drug to a patient's lungs through inhalation.

2. Brief Discussion of Art:

A number of devices are available for delivering a drug into the lungs of a patient. A pneumatic or jet-type nebulizer is particularly effective in supplying an aerosolized drug for inhalation, but other types of nebulizer are also available, such as an ultrasonic type nebulizer in which the drug to be atomized is forced through a mesh by vibrating a piezoelectric crystal, whereupon the droplets passing through the mesh are entrained in the air being inhaled by the patient. The gauge of the mesh determines the size of the droplets which enter the air stream. Alternatively, a dosimetric spacer can be used. When using a spacer, the drug is introduced into a holding chamber of the spacer, either in aerosolized form, or by loading the air within the holding chamber with the drug in powered form. The patient then breathes from the holding chamber, thereby inhaling the drug laden air. Such spacers are particularly effective when treating children or elderly patients, and for use with certain drugs. The drug is normally delivered over a number of breaths. Of course, the concentration of the drug in each breath decreases over time as a result of dilution caused by ambient air entering the holding chamber to replace the air being inhaled by the patient, and as a result of the deposition of the drug within the chamber.

As will be appreciated from this specification, the invention applies to all different types of drug delivery device.

When a doctor prescribes a particular drug for treatment of a patient, the patient not only requires a supply of the drug, but also requires a drug delivery apparatus, for example a nebulizer or a dosimetric spacer. In the case of a nebulizer, the prescribed amount of drug for a treatment is placed in the nebulizer, and in most cases, the patient inhales from the nebulizer repeatedly until the prescribed amount of drug has been delivered. Unfortunately, this is no guarantee of the patient receiving the required dose in his or her lungs. Most of the drug tends to impact in the patient's airways before it reaches the lungs, and some of the drug is exhausted from the lungs on exhalation. Typically, about ten percent of the drug which is delivered by the atomizer reaches the lungs. However, there is a wide variation in the proportion of the drug which reaches the lungs of the patient since the effectiveness of the drug delivery depends on the way in which the patient uses the device. If the patient inhales deeply and regularly, then plenty of the drug will reach the lungs. However, for patients exhibiting symptoms of pulmonary disease, breaths will be shallower and treatment may be interrupted by symptoms of their disease such as coughing. This will substantially reduce the amount of the drug delivered to the patient such that they will not receive as much of the drug as their doctor intends.

More recently, the applicant for this patent has put on the market a nebulizer which calculates the dose of the drug which the patient receives in his lungs. The nebulizer is supplied to the patient pre-programmed with the dose of a particular drug which the patient requires. The patient is prescribed a particular drug, and before use the patient will insert the drug, usually in liquid form, into the nebulizer. The patient then starts inhaling from the nebulizer and the drug is delivered to the patient. The atomizer is arranged such that it only delivers the drug during the first fifty percent of the inhalation phase of the patient, and the flow rate of inhalation of the patient through the device is measured, and from this, the dose of drug received by the patient can be calculated. Once the preprogrammed dose has been delivered, the nebulizer will automatically stop atomizing the drug regardless of whether or not any drug remains within the nebulizer which has not been atomized. The atomizer must be reset before the next dose of the drug is delivered. This device is disclosed in Medic-Aid Limited's earlier patent publication (GB-A2316323), and we hereby incorporate the information contained therein by this reference in its entirety.

Whilst the applicant's product has significantly improved the accuracy of drug delivery, if the patient's doctor wishes to change the dose of the drug delivered to the patient, or to change the prescribed drug altogether, it is necessary to return the nebulizer for reprogramming, or to replace it with one with the correct drug and dose details. In a known drug delivery system, the prescribed drug for each treatment is supplied in separate drug vials, each of which contains the required drug for a single treatment. Thus, a number of vials will normally be supplied to the patient for use one at a time over a period of, typically, one month. In that arrangement, each drug vial carries a bar code thereon such that, before each treatment, the bar code is read by a bar code reader on the atomizer to identify what the drug is which is to be delivered. However, the bar code must be attached to each vial, requiring increased manufacturing costs and also the carrying out of regulatory approval tests to ensure that the adhesives of the label and the dyes used will not contaminate the drug within the plastic vials or reduce the storage life of the product. Long term stability testing over two or three years is required.

According to another prior art arrangement, narcotic drugs are delivered using an atomizer for pain relief. In that case, it is clearly important to restrict access to the use of the drug delivery apparatus with that drug to the patient concerned. The patient is supplied with an I-button which is kept separate from the drug and the atomizer, and which must be touched against a contact surface on an atomizer in order to activate it for a treatment. The button is merely used as a key to unlock the atomizer for a single treatment.

BRIEF SUMMARY OF THE INVENTION

According to a first aspect of the invention, a drug package comprises a plurality of drug vials containing drugs for delivery to a patient in a drug delivery device; and a data carrier including drug treatment information for use by the drug delivery apparatus.

"The drug vials referred to here are suitable containers for holding the drug which is to be administered. Drug vials are manufactured in a number of different configurations, but normally must provide a secure environment which maintains the drug's stability and prevents contamination throughout the specified shelf life. It should normally be convenient for the end user to open. The particular type of vial will be selected for a particular drug on its ability to meets these criteria, and taking account economies of manufacture. The ability to re-program the drug delivery device without returning it is an advantage here. The device can be re-programmed every time a drug is prescribed, if necessary, by a doctor changing the dose on the prescription. Also, the same device can be used for different drugs, in which case the can be changed according to which drug is to be delivered. In this specification, reference is made to a data carrier. The data carrier is used to transfer electronic data between devices by physical translocation of the data carrier. The data carrier is separate from the drug delivery device, and is supplied separately from that device.

Preferably, the drug treatment information includes at least one of the following items of treatment information:
a. the dose of drug to be delivered;
b. the drug which is to be delivered;
c. the expiry date of the drug; and
d. the number of treatments in the package supplied with the data carrier.

Preferably, the drug delivery apparatus is one for delivering the drug in the inhaled air stream to the lungs. The drug delivery device may be an aerosol generator which aerosolizes the drug such that it has a particular size distribution suitable for inhalation, typically in the range of 1 to 5 microns. It is also preferred that the aerosol generator operates to aerosolize the drug during a particular part of the inhalation of a patient in order to maximize lung deposition of the aerosolize drug.

The data carrier is preferably in the form of a button. The data carrier may be moved to a receptive surface or region of the drug delivery apparatus in order to transfer the details the treatment into the nebulizer. Preferably, only one data carrier is supplied in the package, and each time a vial of drug is to be delivered, the data carrier is moved into the region of the drug delivery apparatus to transmit the treatment information to it. The data carrier will normally only transmit the treatment information to the apparatus on a limited number of occasions corresponding to the number of drug vials supplied in the package, or the apparatus will only allow a limited number of treatments to be delivered, corresponding to the number of drug vials.

Preferably, the data carrier is a radio frequency device which is powered inductively from a radio frequency transmitted within the body of the drug delivery apparatus. One of the advantages of using r.f. devices is that the system requires no electrical contacts between the data carrier and the body of the drug delivery apparatus which could be subject to environmental contamination. The data carrier will generate an r.f. signal in return which will be superimposed on the driving r.f. signal from the atomizer, and which is received and decoded by the atomizer.

In addition, it is preferred that information concerning a treatment be transmitted back to the data carrier where it is recorded. Once the pack is finished, the data carrier may be mailed back to the doctor, or transmitted electronically by telephone so that the doctor is able to view how the treatments have taken place and whether or not the patient has been using the drug delivery apparatus correctly.

Since the data carrier is supplied in or on the package with the vials of drug, minimal regulatory difficulties are encountered. In addition, if a patient tries to use an unauthorised drug in the device, the atomizer will not operate. This is important since some drugs, such as Dnase or A1AT, which are protein based drugs, may be damaged if they are contaminated with other drug substances. An atomizer device should only be used for this one drug. In addition, if a drug formulation is not compatible with the plastics used to manufacture the delivery apparatus, if the drug has been identified to the atomizer, it will not operate.

As a result of the use of the data carrier, each vial can contain more drug than is expected to be used so as to allow for inefficiency in the patient's breathing patterns caused by poor breathing technique or by breathing affected by a patient's disease, such as in a MDI spacer system or to paediatric patients. In addition, the use of the vials containing larger amounts of a drug can be manufactured for different treatments. The treatment information with the data carrier controls the dose of the drug delivered. Thus, a single vial size of drug can be manufactured and sold, but the size of dose can vary widely depending on the dose information carried by the treatment information. This results in economies of scale and reduces regulatory submissions.

The treatment information on the data carrier can be decided by, or modified by a physician. The physician may be allowed to alter the dose of the drug to be delivered, or other treatment information. This would require the physician to use a secure interface in order to implement the patient's specific prescription. The dose of drug, for example, can be tailored to the patient for both individual treatments and the frequency of treatments. This is particularly important in systemic applications where the dose of drug in the blood needs to be controlled and tailored to each patient, such as pain control or pulmonary hypertension drugs. The frequency of treatment also needs to be controlled in pain control to prevent overdosing.

According to a further aspect of the invention, a drug delivery apparatus includes a delivery portion for delivering a drug to a patient; an input for receipt of treatment information for each treatment to be administered to a patient; and a nebulizer controller for controlling the amount of drug delivered to a patient on the basis of the treatment information received. Preferably, the input is a radio frequency input which receives the treatment information from a data carrier at radio frequency. Preferably, the input is additionally arranged to transmit completed treatment information to the data carrier for recordal.

Preferably, the atomizer includes an authorisation portion which prevents atomization if any of the treatment information, such as the expiry date of the drug, indicates that the drug is not suitable for delivery.

According to a further aspect of the invention, an electronic data carrier for use with a drug delivery apparatus comprises a memory for holding treatment information concerning the use of the drug delivery apparatus in delivering a specified drug; and an output for transmitting treatment information to the drug delivery apparatus.

According to a further aspect of the invention, a drug delivery system includes a drug delivery apparatus for delivering a specified drug; and a electronic data carrier containing treatment information relating to the specified drug, the data carrier including an output for transmitting treatment information to the drug delivery apparatus before each treatment with the specified drug whereby the drug delivery apparatus delivers the specified drug in conformity with the treatment information.

According to a further aspect, a method of operating a drug delivery apparatus comprises:

supplying a number vials of a drug for use with the drug delivery apparatus;

supply for a data carrier including treatment information;

transmitting treatment information from the data carrier to the drug delivery apparatus;

placing an amount of the drug in the drug delivery apparatus; and delivering the drug in accordance with the treatment information from the data.

BRIEF DESCRIPTION OF THE DRAWINGS

Embodiments of the present invention will now be described with reference to the accompanying drawings by way of example only:

DETAILED DESCRIPTION OF THE INVENTION

Figure 1:
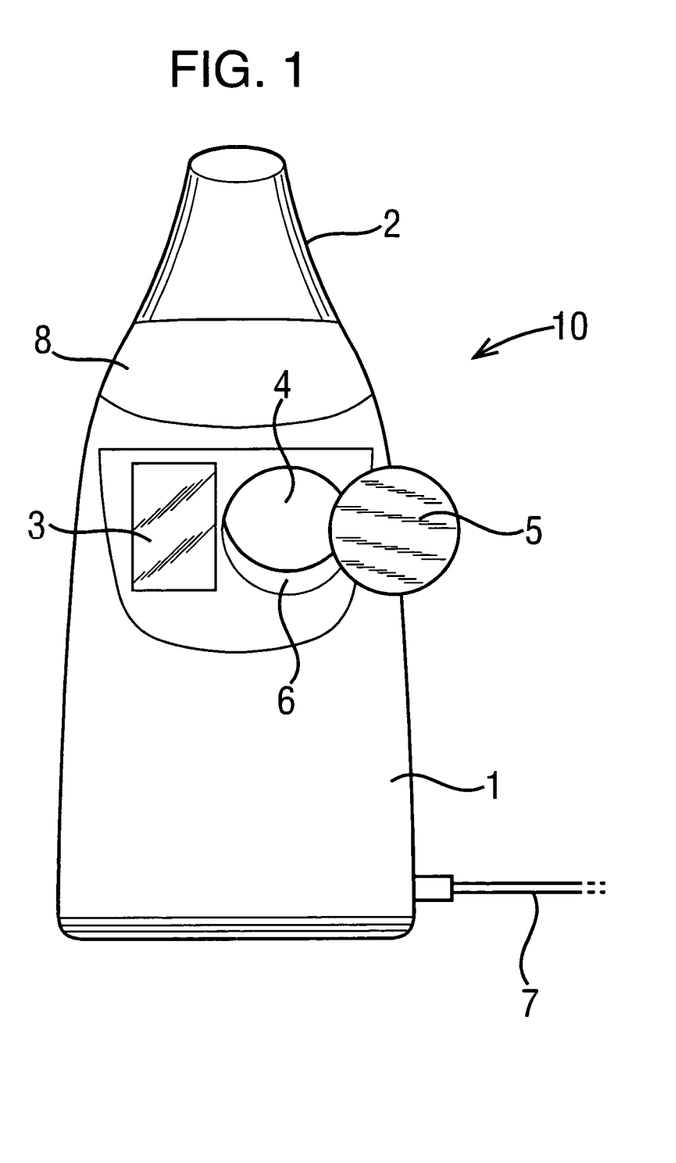
FIG. 1 shows an atomizer for delivery of a drug, including a receptive region, together with a data carrier in the form of a button.

Referring to FIG. 1, a nebulizer 10 is shown including a body 1 and a mouthpiece 2 through which a patient breathes to receive an atomised drug during inhalation. In addition, the nebulizer 10 includes a display 3 for displaying information concerning the use of the machine and the treatment being delivered, and an input 4 in the form of a receptive region in which a data carrier 5 in the form of a button may be placed in order to transmit information concerning the treatment into the device 10.

The nebulizer 10 delivers a drug to a patient in his or her inhaled airstream. The drug is supplied in a package (not shown) including a number of individual containers or vials, each one for use in a separate treatment. Enough vials are supplied for a course of treatments of, typically, one month. The package is supplied with a data carrier 5 inside, or attached to the outside of the package, and the treatment information contained therein relates to the delivery of the drug within the vials with which it is supplied.

In this case, the data carrier 5 includes a small microchip having a memory, to which is connected an aerial. The atomizer 10 includes a radio frequency transmitter connected to a further aerial for generating a radio frequency (RF) signal. When the data carrier 5 is placed in the region 4, the aerial within the button receives the radio frequency signal and generates electric power to operate the microchip. The microchip is then caused to generate an additional RF signal through the aerial in the data carrier 5 which contains treatment information. This is detected with the nebulizer 10, so that the nebulizer receives treatment information from the data carrier 5. In addition, the nebulizer 10 can receive an additional RF signal by which information concerning actual treatments are downloaded into the data carrier memory so that the data carrier 5 may store information concerning actual treatments which may be read and analysed later.

A suitable RF system which can be used is the HiTag made by Phillips, and includes a data carrier button which includes a memory for holding data, and a reader for reading information from the data carrier 5 and for writing data onto the data carrier 5.

The body 1 of the drug delivery apparatus 10 includes a button holder 6 in the form of a wall spaced from the surface of the body 1 adjacent the input 4 to form a pouch in which the data carrier 5 will fit. In this case, the data carrier 5 can be left in the holder 6 for the duration of a treatment, or even for the entire time that the package of drug is in use. To minimize the possibility of loss of the data carrier 5, the button holder 6 includes an interlock to prevent the data carrier 5 from falling out.

Beneath the mouthpiece 2 is a medication chamber 8. The medication chamber 8 includes a reservoir or well (not shown) into which the drug must be poured before the drug delivery device 10 can be operated. Atomization of the drug takes place within the top part of the body 1, and a patient breathes in and out through the mouthpiece 2. On inhaling, drug-laden air is breathed into the lungs. To fill the drug delivery apparatus 10, the mouthpiece 2 is removed, and the drug is poured into the reservoir in the medication chamber 8. The mouthpiece 2 can then be replaced on top of the chamber 8. In the case where the drug delivery device 10 is a nebulizer similar to the HaloLite, an intermediate component must be removed before the drug is poured into the reservoir, and replaced afterwards. After a treatment has been completed, the medication chamber may be removed and emptied of any remaining drug, and washed. If the patient requires treatment using two different drugs, a different medication chamber 8 may be used with the other drug, thereby preventing contamination which might have a detrimental effect on the drugs being used.

In an alternative embodiment, the medication chamber carries the pouch which retains the data carrier 5. The button holder will hold the button over the input region 4. The advantage of this arrangement is that, where a patient has one device, but takes different medications from different medication chambers, the button is automatically changed with the chamber. Different chambers may be required, not only when the drugs are not compatible, but also if different aerosol characteristics are required.

The body includes an air supply line 7, since the nebulizer 10 is pneumatic, and requires a supply of pressure air to drive atomization.

In addition to the body including the drug delivery portion towards the top, beneath the mouthpiece 2, and one half of the radio frequency system, various other parts are contained therein. Although not shown in FIG. 1, there is various electronic circuitry and the like which senses and analyses the treatments which are given, and carry out other functions as are required below.

Figure 2:
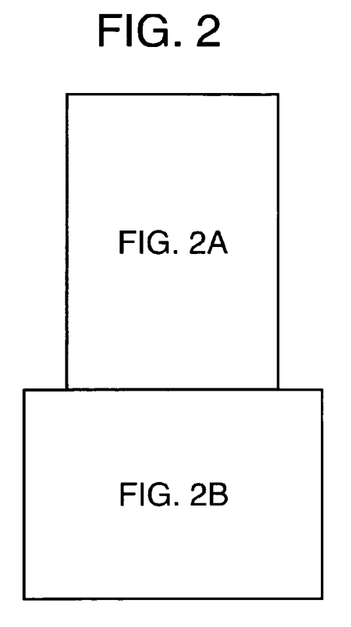
FIG. 2 shows part of a flow diagram of operation of the nebulizer shown in FIG. 1.
Figure 2A:
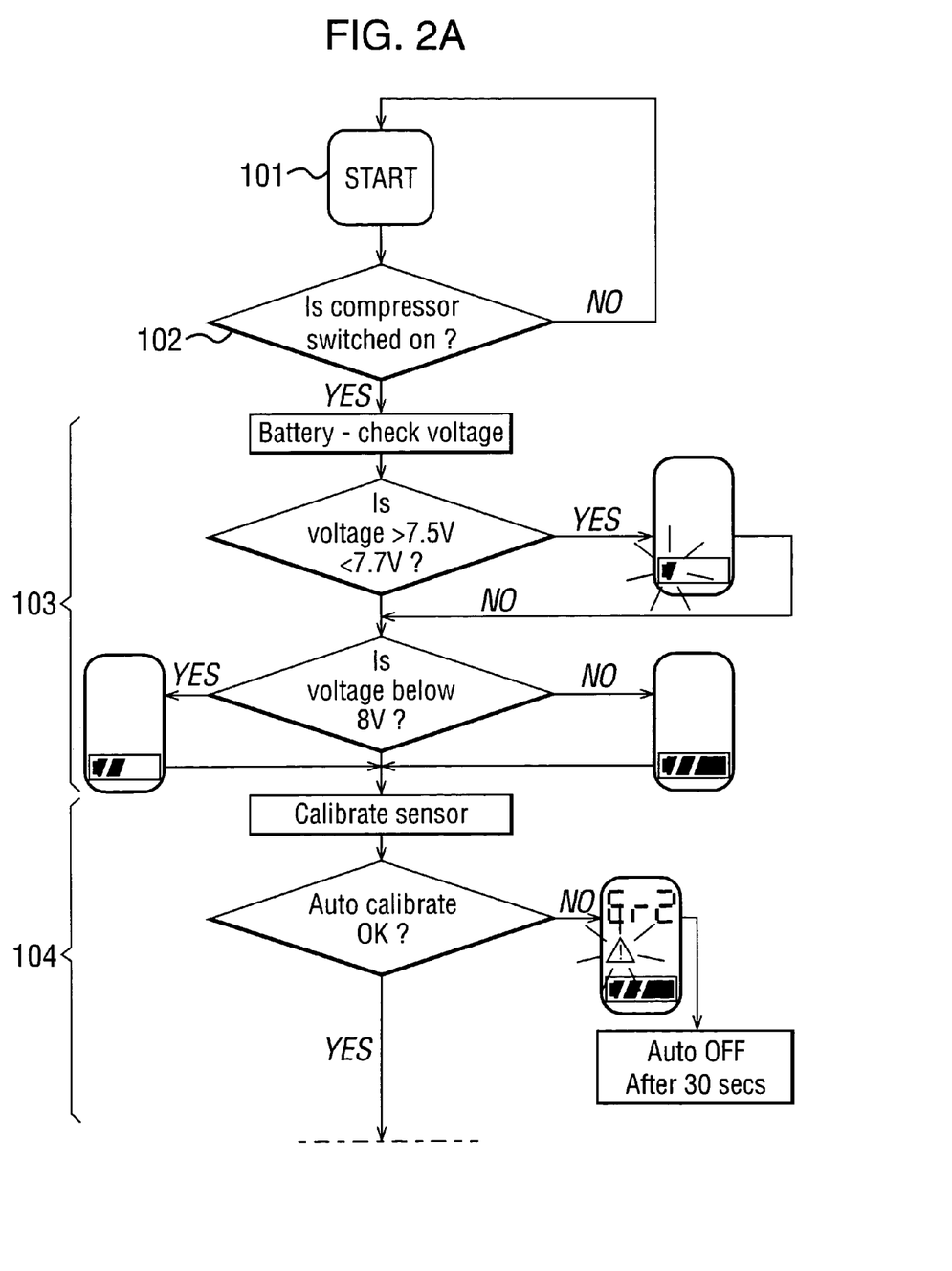
Figure 2B:
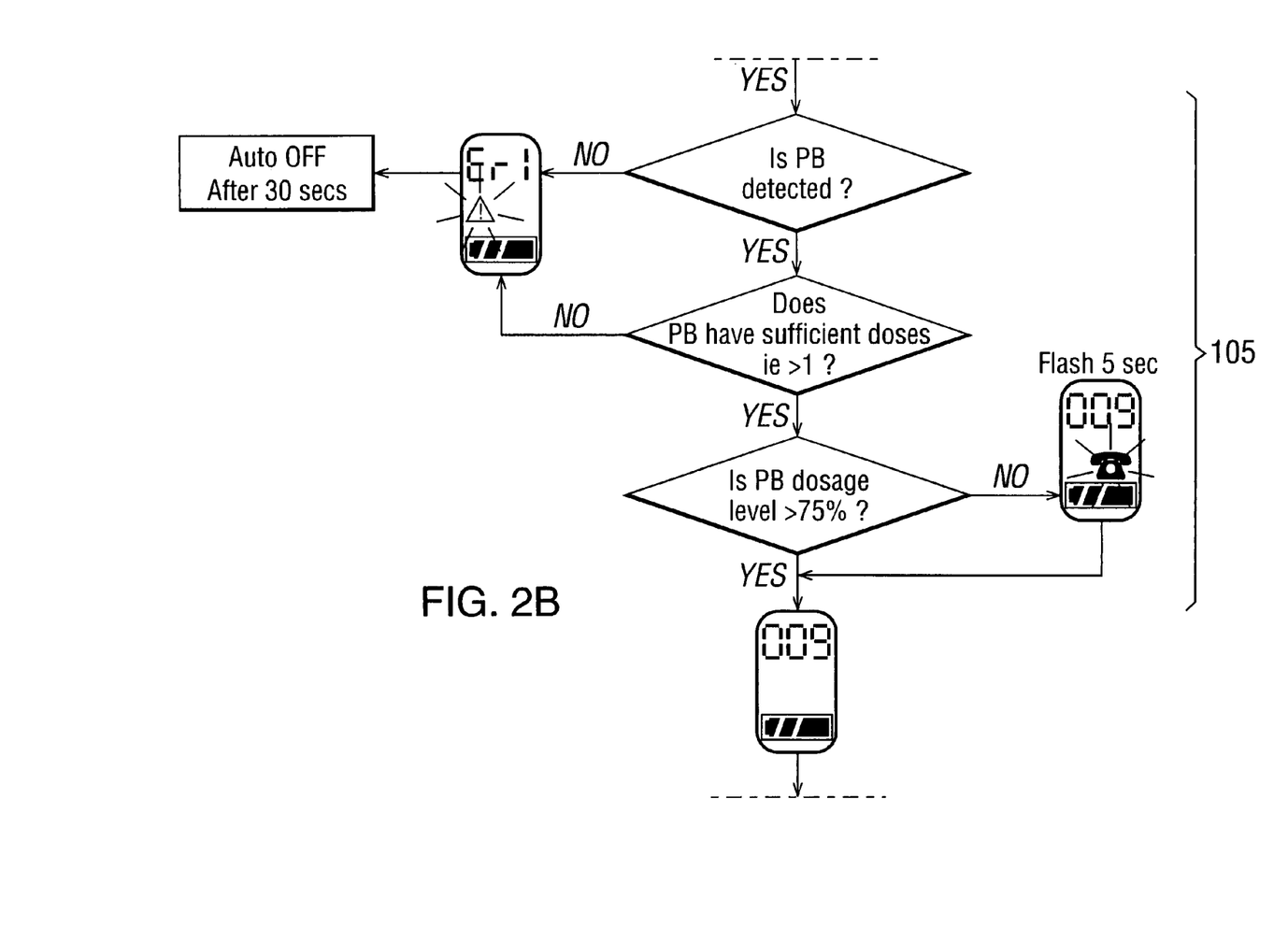
Figure 3:
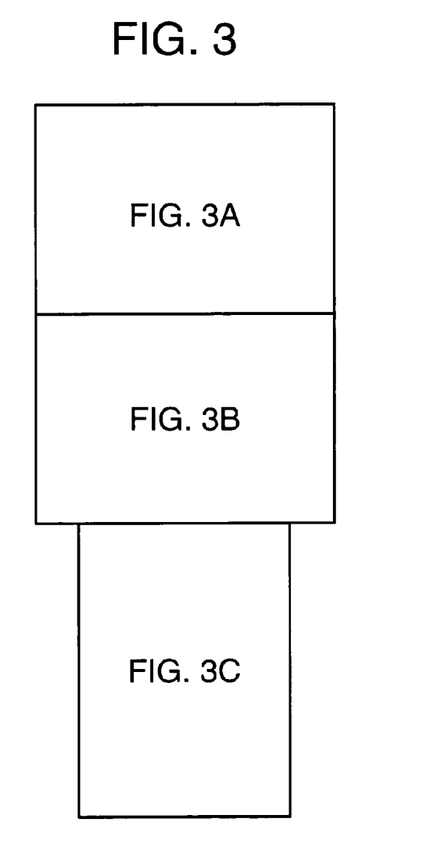
FIG. 3 shows the remainder of the flow diagram shown in FIG. 2.
Figure 3A:
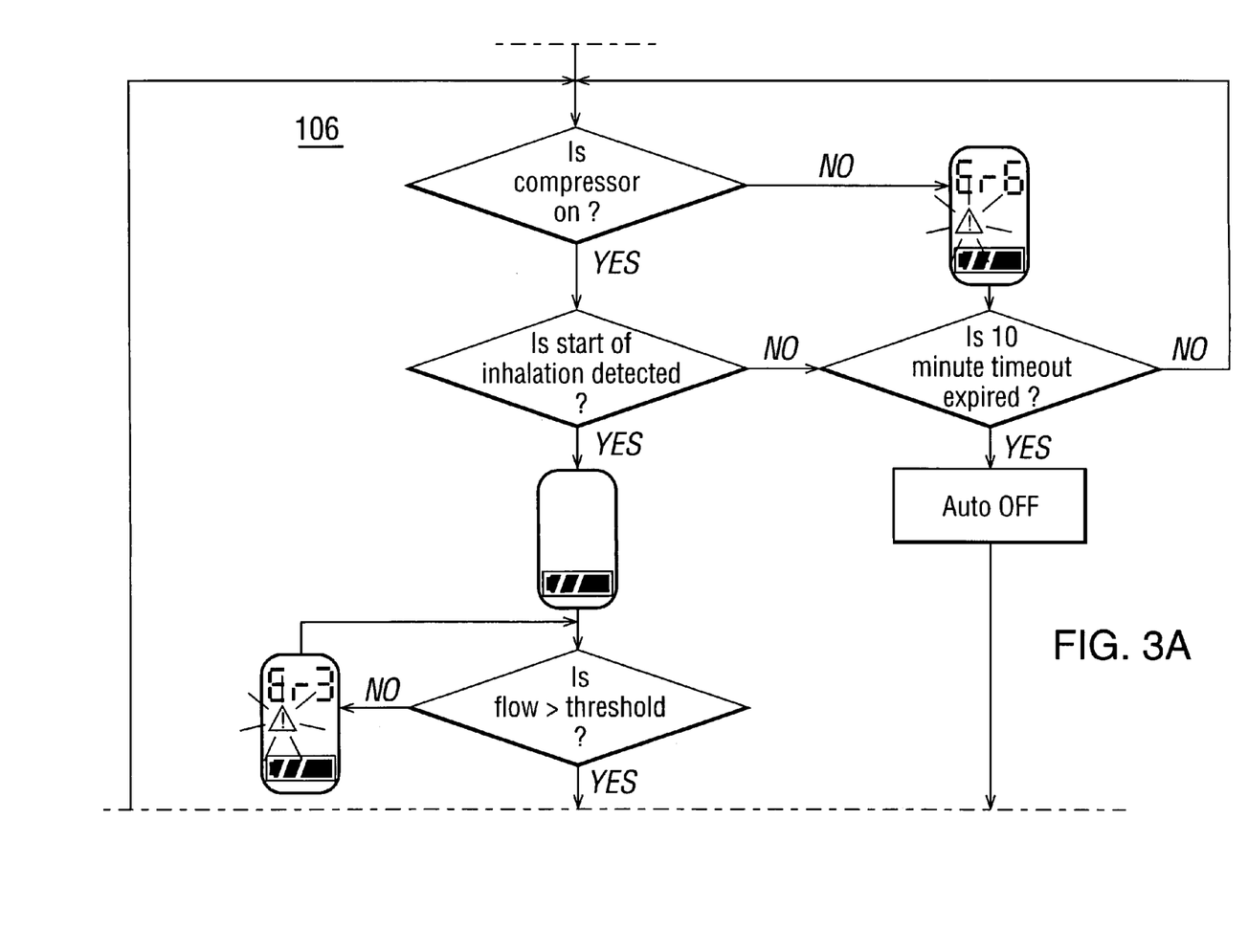
Figure 3B:
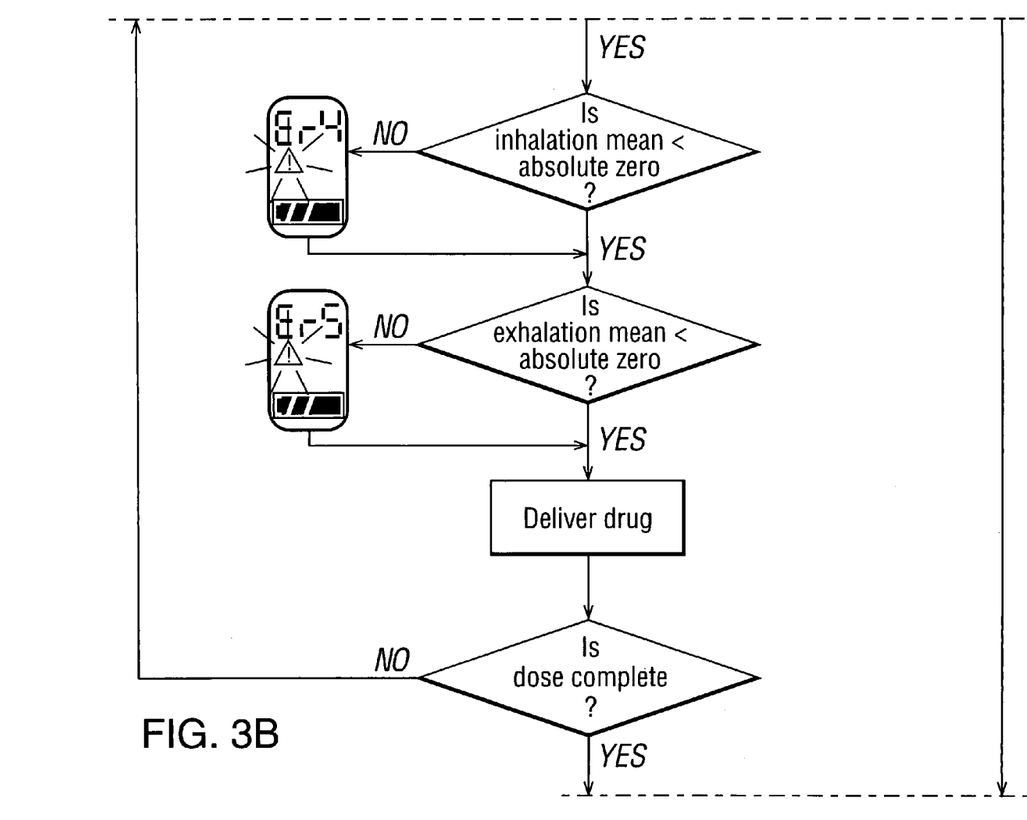
Figure 3C:
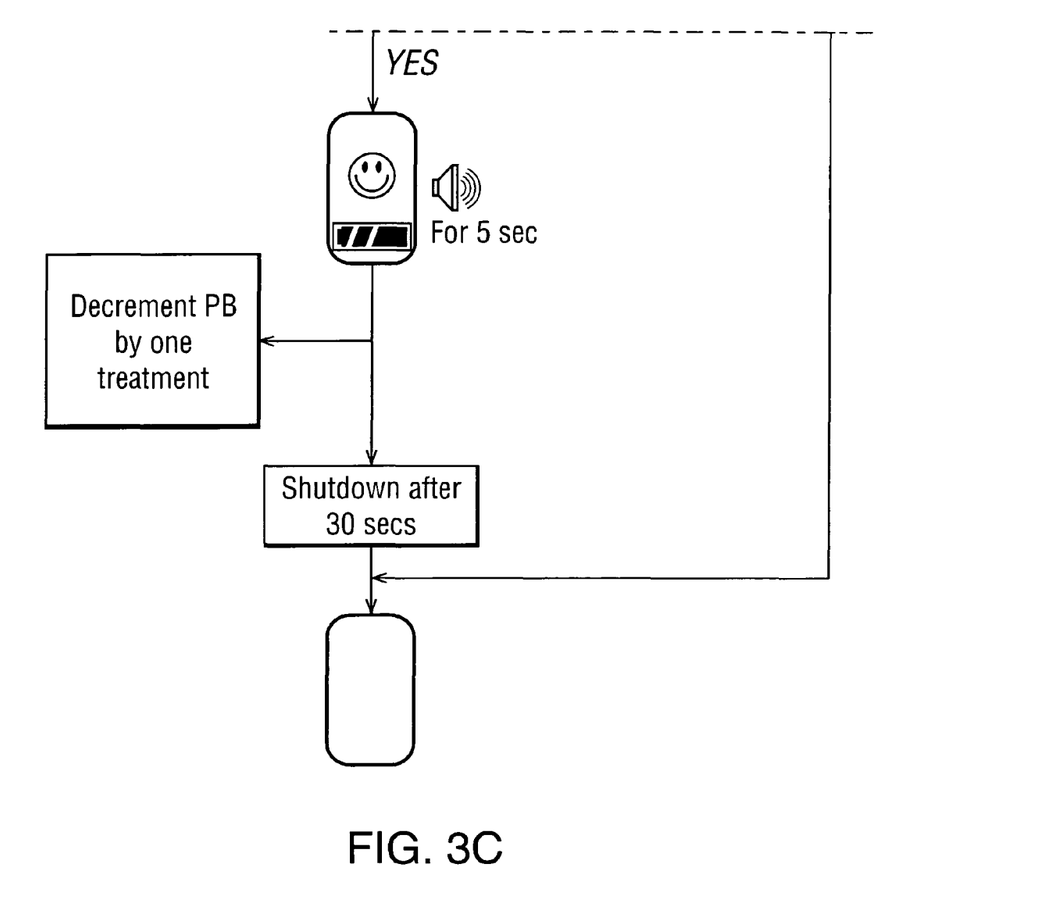

Referring to FIGS. 2 and 3, a flow diagram is shown which indicates the operation of the drug delivery apparatus 10, and its operation in connection with the data carrier 5. Starting at the top of FIG. 2, the logic operations of the drug delivery device 10, which in this case is a pneumatic jet nebulizer starts at 101. A suitable pneumatic nebulizer which can be used is the HaloLite made by Medic-Aid. First, the question 102 is asked whether or not compressed air is being received by the device via air supply line 7. Since it is a pneumatic nebulizer the atomization is generated by compressed air. It cannot operate until a supply of compressed air is received for example, from a pump. Once a pressure detector within the apparatus detects that compressed air is received, the device checks the battery to ensure that sufficient power is supplied to the device. The battery level is detected by a battery charge detector, and is indicated to the patient on the display 3 (see FIG. 1). The next step 104 is the calibration of an airflow sensor within the nebulizer. The operation of this drug delivery device requires that the air flow through the device generated by the breathing of a patient is known, firstly to indicate when a patient starts to inhale whereby the drug may be delivered, and secondly to calculate the dose delivered since the dose delivered is dependent on the rate of airflow through the device.

Calibration takes place automatically, but if calibration fails, that failure is indicated to the patient and the device is switched off shortly thereafter. The next step, 105 is the entry into the drug delivery device of treatment information. The patient is given a period of thirty seconds in which to enter the treatment information by placing the data carrier 5 in the region of a data reader 4 so that the treatment information may be downloaded. In most instances, the data carrier 5 is left in the pouch between treatments, and only needs to be replaced when a new package of a drug is used. Once the treatment information is downloaded, the drug delivery apparatus checks that it has not already delivered all of the supplied doses of that drug. Provided that there are sufficient doses left, then drug delivery can begin. If the number of doses of the drug within the package falls below a certain proportion of the total doses originally supplied, in this case where 75% of the dosages have already been delivered, the patient is prompted to order a new supply, for example by telephone. In this regard, a flashing telephone symbol appears on the display three for five seconds. For example, if the package is supplied with twenty vials, the telephone symbol will flash each time the user seeks to use the last five of the vials. Alternatively, if the nebulizer is arranged to be connected to a telephone line, a request for a new prescription can be passed to a remote computer which will arrange for a new prescription to be issued. Alternatively, a new package of the drug may be delivered directly by mail from the pharmacy on the basis of the request for a new package.

The data carrier 5 contains treatment information of various types, including the number of vials of a drug which was supplied in the package, which corresponds to the number of treatments which can be obtained from that course of treatment. The data carrier is, effectively, a memory device in which, amongst other things, the total number of treatments in the course of treatments is stored. As each treatment is used, those treatments are counted as part of the analysis of the treatment which takes place, and reordering can take place automatically, if for example, a modem is included in the drug delivery apparatus which will connect to the telephone system and will send out a request for another course of treatment to be prescribed. The electronic processor within the drug delivery device monitors and analyses a number of aspects of the treatment, including the number of treatments which have taken place. When more of the drug is required, it can be arranged to send a signal to the part of the processing system which orders a repeat prescription via the modem. Alternatively, some other electronic form of communication can be used, such as an electronic network.

Referring to FIG. 3, which is a continuation of the flow diagram of FIG. 2, the presence of compressed air is again checked at 106, and provided that it is present, the nebulizer will wait for the patient to start inhaling. Provided that the patient inhales strongly enough, the first three breaths are measured using a suitable sensor, such as a pressure sensor to identify the average duration of inhalation, and the drug is then delivered into a subsequent breath for the first 50% of that breath, calculated by averaging the duration of the previous three inhalations. During treatment, the dose delivered by the drug delivery apparatus is continually calculated. Once the total dose reaches that which the patient is supposed to receive, which is included in the treatment information supplied by the data carrier 5, an audible sound is generated, and the device is switched off. In addition, information concerning the treatment which has been carried out can be downloaded on to the data carrier after the treatment, or before the next treatment is started. Such downloaded information might include data on when treatments are given, how long a treatment took to complete, whether treatment was completed or not, the duration of a patient's inhalations during treatment, the flow rate of a patient's inhalations and the like. Furthermore, on completion of delivery of a dose, the drug delivery apparatus decrements the number of treatments left to be supplied by the package of drug associated with that data carrier 5.

The data carrier 5 includes a number of data fields which are programmed into the carrier before it is inserted into a package of drug. These include the number of treatments which can be derived from that drug package, a security code or access code whereby the security code of the data carrier 5 identifies to the drug delivery apparatus so that it may only be used to deliver one set of treatments corresponding to the package of drug with which it is supplied. Fields may be included in the data carrier which can be programmed by the physician to include patient specific parameters. In fact, the treatment information included in the fields of the data carrier could be modified by a physician in order to make the prescription specific to that patient. This may allow the dose of the drug to be tailored to the patient's requirements, both for individual treatments, and the frequency of treatments. This is important in systemic applications where the dose of drug in the blood needs to be controlled and tailored to each patient, such as pain control or pulmonary hypertension. The frequency of treatment also needs to be controlled in pain control to prevent overdosing. The data carrier also includes a drug identification, the dose to be administered in each treatment, and the expiry date of the drugs. In addition, if the data carrier is used to record the delivery of treatments, spare fields can be made available for recording that information. The drug delivery apparatus can download information on to the data carrier, including the serial number of the drug delivery apparatus in order to identify the machine and the patient, the number of treatments used, and other information concerning the treatments. The information concerning the delivery of treatments can then be delivered to the physician who can analyze the treatments to ensure that they are satisfactory. The physician can intervene in the treatment if it is seen that there is some problem. For example, the physician will be able to tell if the patient is not complying with the treatments, or if the patient has not adapted to that particular type of treatment. The patient might be given additional training in the use of the drug delivery system, or different treatments might be deemed to be more suitable for that patient. One of the particular advantages of the physician receiving the information concerning the treatments is that real information concerning the treatments is received by the physician rather than the patient's view of treatment, which can differ significantly. The information concerning the treatments which is downloaded onto the data carrier 5 can be accessed by the physician in several ways. For example, the patient can give the data carrier to the physician if the physician has the appropriate apparatus for reading the information carried on the data carrier, or can be mailed to the manufacturer of the data carrier or some other intermediary who will download the information from the data carrier and transfer the information to the physician. Alternatively, the information can be transferred by telephone from the patient directly to the physician or to some intermediary.

A telephone interface can be supplied whereby the information concerning the delivery of treatments, patient compliance and the like are passed down a telephone line to the manufacturer, the patient's doctor or other intermediary. The information would typically identify the type of drug delivery apparatus, its serial number, the drug identification, the number of treatments of drug used, and any other useful information. The telephone interface can be arranged to receive information concerning treatments which have been carried out either directly from the drug delivery apparatus or from the data carrier 5. If the information is passed directly from the drug delivery apparatus, it would typically be connected to the telephone interface by a simple data cable connection, but if the telephone interface receives the treatment information from the data carrier 5, it will need to include a reader to download the information from the data carrier. Such a reader would be technically similar to the radio frequency transmitter of the atomizer, described above. The treatment information can then be transferred down the telephone line either directly to the physician, or via an intermediary which might be a database administered by an intermediary. The database might be accessed directly by telephone, or via the internet. Either way, the patient's physician will have access to the information concerning the treatments which have been delivered, and will be able to take any necessary action as a result. For example, if it is clear that the patient is not complying with the treatments prescribed, or is unable to operate the apparatus properly, the physician may intervene by contacting the patient. In addition, reference is made above to the drug delivery apparatus identifying when only a certain proportion of the vials in the drug package remain and indicating to the patient that more must be ordered. The use of the telephone interface will allow the information concerning the treatments which have been received by the patient to include an indicator that a repeat prescription is required. This can then be passed down the telephone line to the intermediary or to the physician whereby a new prescription can be prepared and forwarded to the patient, or a new drug package of vials containing the drug can be sent directly to the patient.

The use of the data carrier 5 in this way has a number of different advantages. Firstly, it can prevent the use of unauthorised drugs in that drug delivery apparatus. This is advantageous for two reasons. Firstly, protein based drugs as rhD-Nase or A1AT may be damaged if they are contaminated with other drug substances. Therefore, any drug delivery apparatus delivering one of these drugs should only be used for that one drug, and no other. In addition, the dose programmed into the drug delivery apparatus for a different drug may not be appropriate for all drug substances. Thus, the chance of the wrong dose being delivered to the patient is minimised. Also, some drugs may not be compatible with the drug delivery apparatus concerned, for example with the plastics used to manufacture the device.

In addition, rather than the amount of drug delivered being controlled by the nominal volume of drug in the vial all of which would often be delivered, the amount delivered is controlled by the dose treatment information in the data carrier. This is important since it allows more drug to be included in the vial than is normally needed to take account of inefficiency in the patient's breathing patents, but delivery will stop once the correct dose is calculated to have been delivered, before all of the drug in the vial has been atomised. It also means that different drug doses can be prescribed to the patient using the treatment information in the data carrier, but that one vial concentration and volume can be manufactured and sold for all of these different doses, thus optimising economies of scale and reducing regulatory submissions. In the past, it would have been necessary to supply different concentrations or different volumes of a drug depending on the amount prescribed. The use of the data carrier 5 means that fewer volumes and concentrations of a drug need to be manufactured.

The data carrier 5 is also able to record information concerning patient compliance with his regimen, and can even drive a direct prescription. A doctor can be confident in the information received from the drug delivery apparatus 10 which is recorded on the data carrier 5. The doctor does not need to rely on the patient's own reports of compliance nor their inhalation efficiency.

Since the data carrier 5 is supplied with a number of vials of a drug, different styles of packs can be used for different therapeutic applications. Some drugs must be supplied in a plastic unit dose vial, and others must be supplied in two-part packages for reconstitution at the point of use. Both of these drug vials can be accommodated because the data carrier is attached to the outside of the box, and contains the dosing information for the whole pack of the drug, typically one month. It is not attached to individual drug vials, and minimises the packaging, regulatory and development requirements for integrating the drugs into the drug delivery system. It avoids potential contamination problems on drug packs, which is a significant issue where labels or printing are applied to plastic vials and lengthy stability tests are required to ensure there is no leaking of dyes or adhesives into the drug over the storage life of the product, which may be up to two years.

Figure 4A:
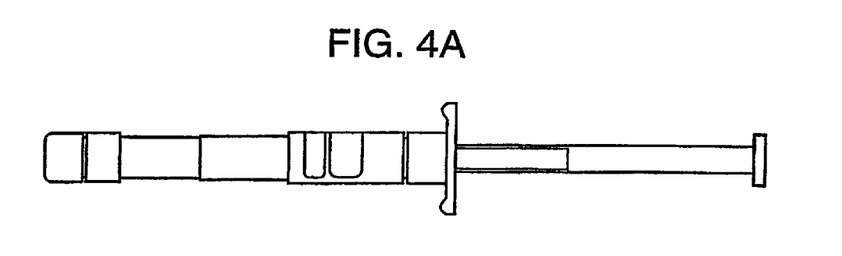
FIG. 4 shows suitable types of drug vials.

FIGS. 4a to 4f show a number of different types of vials which should be suitable for use in carrying out this invention. FIG. 4a is a dual compartment vial for holding two different components apart until the drug is ready to be dispensed. The two substances can then be mixed immediately prior to use. For example, one compartment might contain a liquid and the other a powder which when mixed together dissolves the powder into the liquid or both compartments could contain liquids which are mixed into the substance to be delivered. Such packages are generally known in this field, and often involve the rotation of the plunger in order to break the seal between the two compartments.

Figure 4B:
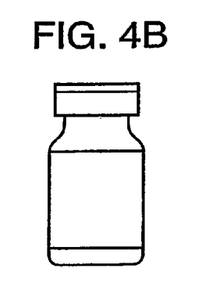

The vial in FIG. 4b is a glass vial with an elastomeric stopper. It is designed to hold liquids or powders.

Figure 4C:
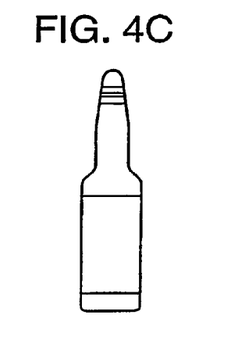
Figure 6:
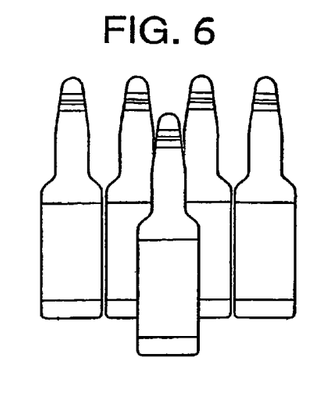
FIG. 6 shows a plurality of vials of the type shown in FIG. 4C.

FIG. 4c shows a glass vial containing liquid. The top of the vial is snapped off to allow access to the liquid. FIG. 6 shows a plurality of this type of glass vial.

Figure 4D:
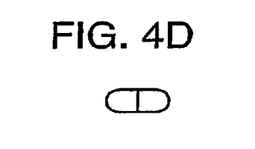

FIG. 4d shows a gelatine capsule for holding powders for inhalation. The gelatine capsule must be broken in order to gain access to the powder.

Figure 4E:
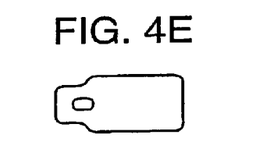

FIG. 4e shows a foil blister pack for holding powdered drug.

Figure 4F:
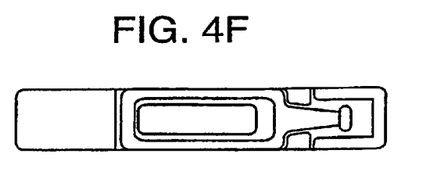

FIG. 4f shows a polyethylene blow fill seal vial for holding a liquid drug.

Of course, vials are not limited to these examples, which are entirely illustrative of vials generally.

The drug may also be packaged in part of the aerosol generation system, as opposed to a separate vial, such as in the nebulizer chamber, or medication chamber. This is a benefit to the patient from ease of use, since the drug dose does not have to be transferred to the chamber in order for treatment to take place, and the chamber is disposed of after the treatment, avoiding the need for cleaning and the potential for contamination. In this case, the medication chamber or the like actually constitutes a vial suitable for holding and transporting the drug.

It should be understood that the embodiment described above is an example of the invention, and that this patent is not limited to it. For example, other drug delivery apparatus can be used, and other types of nebulizers, such as piezo-electric and ultrasonic nebulizers or powder delivery systems such as a dosimetric spacer. Also, the data carrier could be one which requires electrical contact to take place in order to transfer data, such as an I-button.

Figure 5:
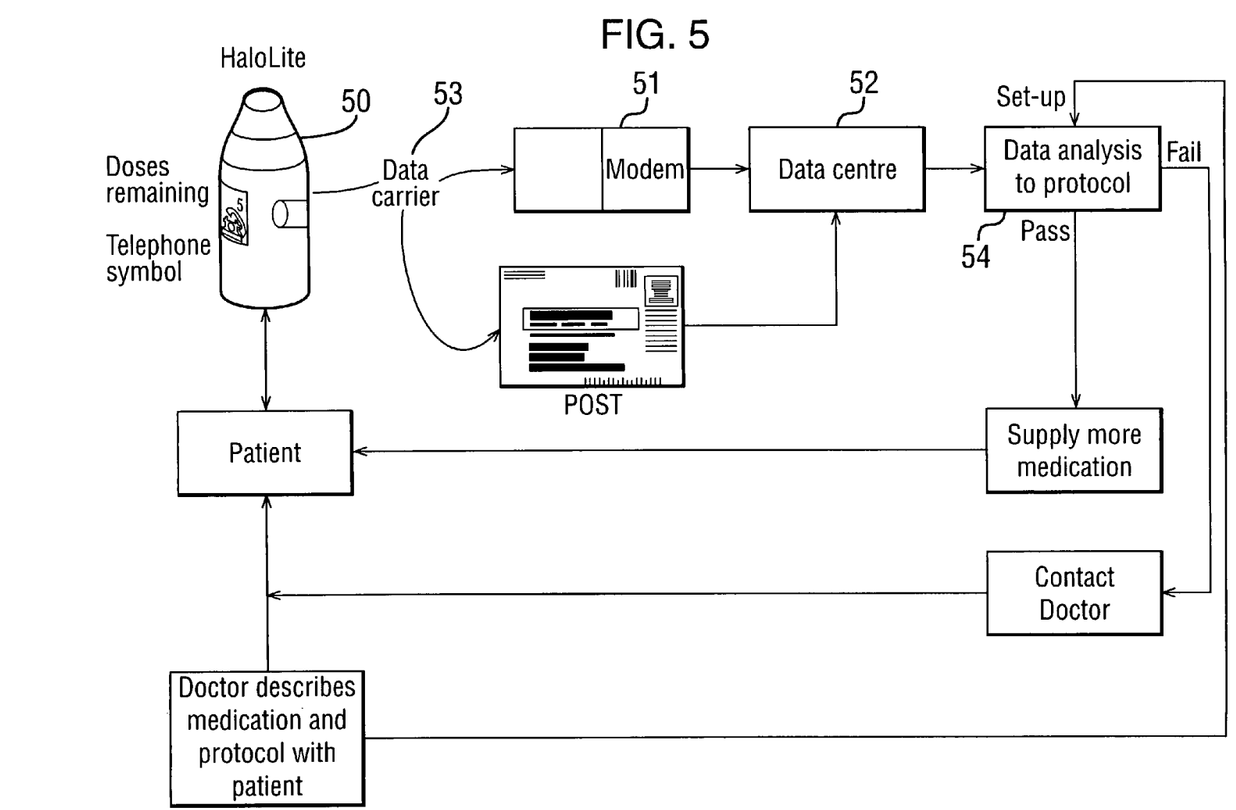
FIG. 5 is a flow chart showing how the drug delivery device can be controlled to drive prescription.

FIG. 5 is a flow diagram showing how the data collected by the drug delivery device can be returned to a data centre for analysis. The data centre could be located at the local hospital or clinic, but is most likely to be centralised with the results of the processing being sent to the clinician responsible for the patient. Initially, the doctor will prescribe some medication and agree a protocol for treatment with the patient. This will be used to initiate the supply of the product to the patient and set the processing by the data centre. Each time the patient returns information via the data carrier or via a communications link, analysis takes place, and if everything is proceeding satisfactorily, more medication is supplied to the patient, but if there is something which seems unsatisfactory in the data, the doctor is contacted to discuss the treatment with the patient.

In FIG. 5, The drug delivery device 50, in this case a Halolite made by Medic-Aid Limited, is used by the patient, and from time to time a modem 51 is used to pass treatment information back to the data centre 52, either directly or by placing the data carrier 53 in the modem. Alternatively, the data carrier 53 is posted to the data centre 52. The data is analysed at step 54, and if the result is satisfactory, more drug is supplied, either by the issue of a prescription, or by the direct dispensing of more of the drug. If the result is not satisfactory, the doctor is contacted, and he or she can contact the patient to identify problems.

What is claimed is:

1. A drug delivery device comprising:
   a delivery portion for delivering a drug to a patient;
   an electronic input arranged remotely from the delivery portion and configured to receive treatment information from a removable electronic data carrier wherein the input is a radio frequency receiver configured to receive the treatment information from the electronic data carrier over a radio frequency signal, wherein the electronic input is additionally configured to transmit treatment information to the electronic data carrier for recordal; and
   a delivery controller configured to control the amount of the drug delivered to the patient based on received treatment information.

2. A drug delivery device comprising:
   a delivery portion for delivering a drug to a patient;
   an electronic input arranged remotely from the delivery portion and configured to receive treatment information from a removable electronic data carrier wherein the input is a radio frequency receiver configured to receive the treatment information from the electronic data carrier over a radio frequency signal;
   a delivery controller configured to control the amount of the drug delivered to the patient based on the received treatment information; and
   an authorization portion which prevents delivery if any of the treatment information indicates that the drug is unsuitable for delivery.

3. A drug delivery system comprising:
   a drug delivery device for delivering a drug, the drug delivery device having a medication chamber for receiving a drug for delivery and an electronic input for receiving treatment information relating to the drug; and
   an electronic data carrier removable from the drug delivery device including a memory for storing the drug treatment information for use by the drug delivery device, the carrier also includes an output for transmitting the treatment information to the electronic input,
   wherein the input is a radio frequency input which is configured to receive the treatment information from the electronic data carrier over a radio frequency signal, whereby the drug delivery device is configured to deliver the drug in conformity with the treatment information,
   wherein the drug delivery device comprises a nebulizer.

4. A drug delivery device comprising:
   a delivery portion for delivering a drug to a patient;
   an electronic input arranged remotely from the delivery portion and configured to receive treatment information from a removable electronic data carrier wherein the input is a radio frequency receiver configured to receive the treatment information from the electronic data carrier over a radio frequency signal, wherein the electronic input is configured to transmit treatment information via a radio frequency signal to the removable electronic data carrier; and
   a delivery controller configured to control the amount of the drug delivered to the patient based on the received treatment information.

* * * * *